(12) United States Patent
Jensen et al.

(10) Patent No.: US 9,168,160 B2
(45) Date of Patent: Oct. 27, 2015

(54) IMPLANTABLE MEDICAL DEVICE WITH FENESTRATION AND RADIOPAQUE MARKER COILS ON STENTS

(71) Applicant: Cook Medical Technologies LLC, Bloomington, IN (US)

(72) Inventors: Kim Moegelvang Jensen, Frederiksberg (DK); Erik E. Rasmussen, Slagelse (DK)

(73) Assignee: Cook Medical Technologies LLC, Bloomington, IN (US)

( * ) Notice: Subject to any disclaimer, the term of this patent is extended or adjusted under 35 U.S.C. 154(b) by 42 days.

(21) Appl. No.: 13/753,866

(22) Filed: Jan. 30, 2013

(65) Prior Publication Data
US 2013/0197627 A1 Aug. 1, 2013

(30) Foreign Application Priority Data
Feb. 1, 2012 (GB) .................................. 1201749.7

(51) Int. Cl.
| *A61F 2/07* | (2013.01) |
| *A61F 2/856* | (2013.01) |
| *A61F 2/06* | (2013.01) |
| *A61F 2/89* | (2013.01) |

(52) U.S. Cl.
CPC . *A61F 2/856* (2013.01); *A61F 2/07* (2013.01); *A61F 2/89* (2013.01); *A61F 2002/061* (2013.01); *A61F 2002/075* (2013.01); *A61F 2250/006* (2013.01); *A61F 2250/0098* (2013.01)

(58) Field of Classification Search
CPC .............................................. A61F 2250/0098
USPC ...................................... 623/34, 35, 1.34, 135
See application file for complete search history.

(56) References Cited

U.S. PATENT DOCUMENTS

| 5,628,783 | A | * | 5/1997 | Quiachon et al. ............ 623/1.35 |
| 5,653,743 | A | | 8/1997 | Martin |
| 5,669,924 | A | * | 9/1997 | Shaknovich ................. 623/1.11 |
| 5,824,042 | A | | 10/1998 | Lombardi et al. |
| 6,344,056 | B1 | * | 2/2002 | Dehdashtian ................ 623/1.35 |
| 6,395,018 | B1 | * | 5/2002 | Castaneda .................... 623/1.13 |
| 6,464,720 | B2 | * | 10/2002 | Boatman et al. ............. 623/1.15 |
| 6,524,335 | B1 | | 2/2003 | Hartley et al. |

(Continued)

FOREIGN PATENT DOCUMENTS

| EP | 0894503 E2 | 2/1999 |
| WO | 95/21592 | 8/1995 |

(Continued)

OTHER PUBLICATIONS

PCT/US2013/023761 Int'l Search Report Cook Medical Technologies LLC Apr. 19, 2013.

(Continued)

*Primary Examiner* — Jacqueline Woznicki
(74) *Attorney, Agent, or Firm* — Richard J. Godlewski; Taiwoods Lin

(57) ABSTRACT

A fenestrated implantable medical device, such as a stent graft (10) is provided with a plurality of zigzag stents (12) of which two or more form fenestrations (34, 36) using part of the stents (12) as a support frame (30, 32) for the fenestrations (34, 36). The frames (30, 32) are preferably covered by radiopaque wire (44) coiled around the stent structures. The radiopaque coil (44) provides easy reference to the fenestrations (30, 32) for imaging purposes.

20 Claims, 2 Drawing Sheets

(56) References Cited

U.S. PATENT DOCUMENTS

| | | |
|---|---|---|
| 8,353,943 B2 * | 1/2013 | Kuppurathanam et al. ..... 623/1.1 |
| 2001/0027339 A1 * | 10/2001 | Boatman et al. ............. 623/1.15 |
| 2002/0042650 A1 * | 4/2002 | Vardi et al. .................. 623/1.35 |
| 2002/0156516 A1 * | 10/2002 | Vardi et al. .................. 623/1.11 |
| 2002/0193872 A1 * | 12/2002 | Trout et al. .................. 623/1.34 |
| 2003/0074049 A1 * | 4/2003 | Hoganson et al. ........... 623/1.13 |
| 2004/0078071 A1 * | 4/2004 | Escamilla et al. ........... 623/1.11 |
| 2004/0167619 A1 * | 8/2004 | Case et al. .................. 623/1.34 |
| 2005/0131518 A1 * | 6/2005 | Hartley et al. ............... 623/1.13 |
| 2006/0195177 A1 | 8/2006 | Kaufmann et al. |
| 2009/0005858 A1 * | 1/2009 | Young et al. ................. 623/1.34 |
| 2009/0048663 A1 * | 2/2009 | Greenberg ................... 623/1.35 |
| 2009/0157164 A1 | 6/2009 | McKinsey |
| 2010/0161025 A1 * | 6/2010 | Kuppurathanam et al. .. 623/1.13 |
| 2011/0190868 A1 | 8/2011 | Ducke et al. |
| 2011/0270373 A1 * | 11/2011 | Sampognaro et al. ....... 623/1.11 |

FOREIGN PATENT DOCUMENTS

| | | |
|---|---|---|
| WO | 03/082153 A2 | 10/2003 |
| WO | 2005/034810 A1 | 4/2005 |
| WO | 2010/030370 | 3/2010 |
| WO | 2011/100290 A1 | 8/2011 |

OTHER PUBLICATIONS

PCT/US2013/023761 Written Opinion Cook Medical Technologies LLC Apr. 19, 2013.

* cited by examiner

IMPLANTABLE MEDICAL DEVICE WITH FENESTRATION AND RADIOPAQUE MARKER COILS ON STENTS

TECHNICAL FIELD

The present invention relates to an implantable medical device and to a method of forming such a device. In the preferred embodiment, the device is designed to have a fenestration and is provided with a radiopaque marker at the zone of the fenestration.

BACKGROUND ART

Implantable medical devices having one or more fenestrations are well known in the art. For instance, fenestrated stent grafts are known for placement across the iliac arteries, by the aortic arch arteries and so on. The fenestrations may simply provide openings for side passage of blood passing through the main lumen of the stent graft, but are also known as couplings for side branches to the medical device.

A fenestrated medical device must be positioned accurately, not only in a longitudinal position in the vessel but also in the correct rotational position so that the or each fenestration is correctly aligned with its associated branch vessel or other feature. As such medical devices are more conveniently deployed endoluminally, it is necessary to be able to visualise the device through imaging during the deployment procedure. As the principal components of the device, typically stents and graft material, are not particularly visible under such imaging, it is common to provide on such devices radiopaque markers such as gold tabs or the like. Traditionally, such markers have been attached to the graft material, for instance by suturing.

It is also known to provide fenestrations with strengthening rings around the apertures in the graft material, such strengthening rings for instance being in the form of one of more turns of wire. A radiopaque marker may be provided on the strengthening ring.

Examples of prior art devices can be found, for example, in US-2011/0190868, WO-2010/030370, WO-95/21592, U.S. Pat. No. 5,653,743, US-2009/0157164, U.S. Pat. Nos. 6,524,335 and 5,824,042.

Known structures of fenestrated medical devices involve the provision of a multitude of components which require relatively involved assembly procedures.

DISCLOSURE OF THE INVENTION

The present invention seeks to provide an improved implatable medical device, such as a fenestrated stent graft or the like.

According to an aspect of the present invention, there is provided an implantable medical device, which device includes a longitudinal dimension and at least first and second stent elements disposed in series along the longitudinal dimension of the device, the first and second stent elements being generally annular and at least one being at least partially curved in a direction transverse to said longitudinal dimension, said curvature delimiting a frame between the first and second stent elements; and a coil of radiopaque material wound around at least a part of said frame.

In the preferred embodiment, the frame delimits a fenestration in the device, the fenestration being in one embodiment preformed in the medical device and in another embodiment being formed in situ, by cutting of the graft material within the area delimited by the frame.

This structure can thus provide a fenestrated device using as the frame of the fenestration the stents which would normally be included as a part of the device and which perform the function of maintaining the shape and position of the device when deployed, as well as a radiopaque marker which in effect forms a part of the stent structure rather than as separate components. The structure thus can avoid additional components in the device and additional assembly steps.

The radiopaque coil can also be used in other embodiments as a measurement marker, whether or not the device is fenestrated.

Preferably, at least one of the first and second stent elements has a wave shape in the longitudinal dimension, said frame being formed by a part of said wave which extends away from the other of said first and second stent elements.

Advantageously, both of said first and second stent elements have a wave shape in the longitudinal dimension, the first and second stents being rotationally aligned with respect to one another such that their wave shapes converge and diverge relative to one another substantially at the same radial positions, thereby to provide a frame at a position at which the wave shapes both diverge away from each other.

In a preferred embodiment, the stent element has a wave shape has said wave shape over the entire of the circumferential extent thereof, having for instance one of a sinusoidal or zigzag shape.

Such stents exhibit good compressibility for delivery purposes and, in accordance with the structure disclosed herein, a fenestration formed by the stents themselves.

Advantageously, a graft element may be attached to the at least first and second stent elements, the fenestration providing an opening in the graft within the frame. The device could thus be a stent graft, for example.

There is preferably provided a sleeve of graft material integral with the fenestration, the sleeve advantageously extending into the device and optionally extending along the longitudinal direction of the device. The sleeve provides a secure coupling and guide for a side branch and can also provide a guide conduit for delivery apparatus.

It is preferred that the first and second stent elements are spaced from one another. The frame of the fenestration may thus be formed of two parts which are unconnected to one another, in the preferred embodiment being formed also by the aperture in the graft material.

The coil of radiopaque material is preferably made of gold. In other embodiments, the coil of radiopaque material may be made of silver, platinum or tantalum.

In a practical embodiment, the coil has tight pitch turns such that the turns of the coil touch one another for substantially the entire length of the coil. This provides a number of advantages. First, tight turns causes these to extend substantially transversely of the struts of the stent, reducing their impact on the characteristics of the stent, such as compressibility and flexibility. Secondly, the turns can form a substantially continuous cover over the part of the stents they overlie, optimising visibility under imaging.

Advantageously, the coil is formed of a wire having a diameter of between 0.05 and 0.5 millimeters, preferably of between 0.1 and 0.2 millimeters. In the preferred embodiment, the coil is formed of a wire having a diameter of around 0.15 millimeters.

The stent elements may be made of a shape memory material, such as nickel titanium alloy. Stents of such a nature are able to be compressed tightly onto a deployment assembly and can subsequently expand to fit within a patient's vessel.

The structure taught herein also provides a readily compressible fenestration structure with radiopacity, all benefiting from these advantages.

According to another aspect of the present invention, there is provided a method of making an implantable medical device, which device includes a longitudinal dimension and at least first and second stent elements, the first and second stent elements being generally annular and at least one being at least partially curved in a direction transverse thereto, the method including the steps of disposing said first and second stent elements in series along the longitudinal dimension of the device; orienting said first and second stent elements relative to one another such that said partial curvature delimits a frame between the first and second stent elements; and disposing a coil of radiopaque material around at least a part of said frame.

Advantageously, the method forms a fenestrated medical device, in which the frame delimits a fenestration in the device, the fenestration in one embodiment being formed at the time of manufacture and in another embodiment being formed in situ by cutting graft material of the device.

Preferably, the step of disposing said coil around at least a part of said frame includes: providing at least one of said first and second stent elements as an open wire element, sliding the coil over said at least one stent element, and closing said at least one stent element to form an annular ring with the coil wound thereon.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

Figure 1:
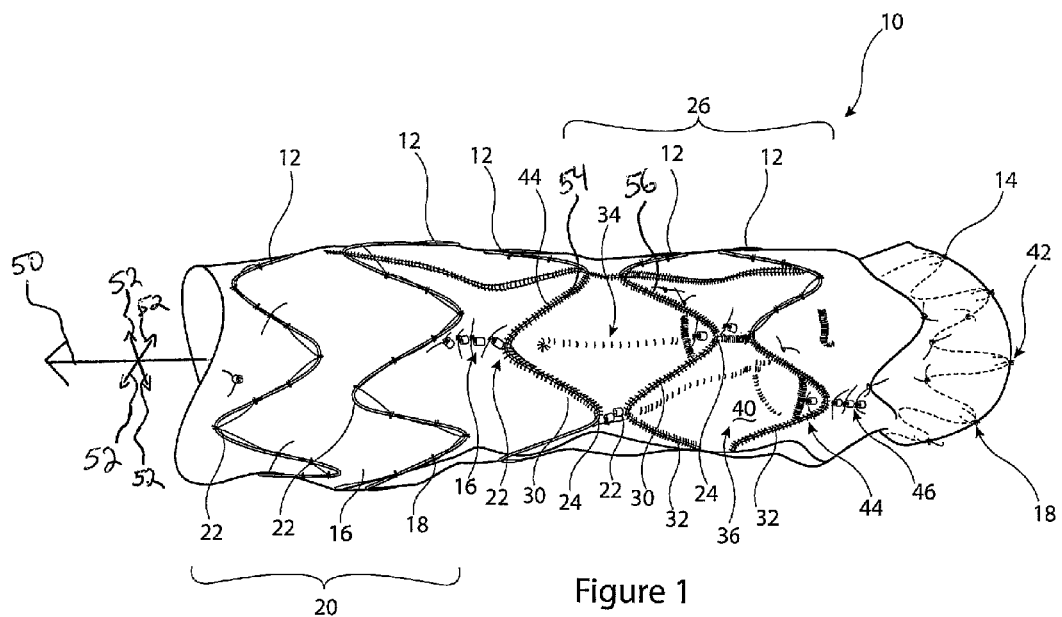
FIG. 1 is a side elevational view of the major portion of an embodiment of stent graft.

It is to be understood that the drawings are schematic only and are not to scale. They are of a form which is intended to facilitate the understanding of the teachings herein.

The embodiments described below are directed to a stent graft having two fenestrations within the graft tubing. It is to be understood that the number of fenestrations in the stent graft can be different and may vary, for instance from a single fenestration to a plurality of fenestrations. Furthermore, the fenestrations need not necessarily be on the same side of the graft tubing. They could be on different sides, for example being opposite one another, for instance to provide access iliac arteries.

It is also to be understood that the teachings herein are not limited to a stent graft and are equally applicable to other types of medical device including, for example, occluders, vena cava filters, and so on. Although the described embodiments are to fenestrated devices, it is to be understood that the teachings herein are not limited to devices which have fenestrations produced at the time of manufacture of the device. The fenestrations could equally be produced in situ during the implantation procedure, for instance by cutting of the graft material within the area delimited by the frame. In other embodiments, the device may have no fenestrations, the frame being used for orientation and/or positioning and/or measurement purposes.

According to an aspect of the present invention, there is provided an implantable medical device 10, which device includes a longitudinal dimension 50 and at least first 54 and second 56 stent elements 12 disposed in series along the longitudinal dimension 50 of the device, the first 54 and second 56 stent elements 12 being generally annular and at least one being at least partially curved in a direction transverse 52 to said longitudinal dimension, said curvature delimiting a frame 30 between the first 54 and second 56 stent elements 12; and a coil of radiopaque material 44 wound around at least a part of said frame 30.

In the preferred embodiment, the frame delimits a fenestration 34 in the device 10, the fenestration being in one embodiment preformed in the medical device 10 and in another embodiment being formed in situ, by cutting of the graft material 16 within the area delimited by the frame 30.

Referring to FIG. 1, there is shown a part of an embodiment of stent graft 10 according to an embodiment of the present invention. The stent graft 10 includes a plurality of stent elements 12 arranged in series along a longitudinal dimension 50 of the stent graft 10. In this example, the end-most stents 14 at both ends of the stent (only one end being shown in FIG. 1) are located on the inside of the graft tubing 16. By contrast, the intermediate stents 12 are located on the outside of the graft tubing 16. The stents 12, 14 may be secured to the graft tubing 16 by means of suture ties 18, in well a known manner. It is to be appreciated that the internal/external positioning of the stents 12 and the manner in which they are attached to the graft tubing 16 are not pertinent to the teachings herein and thus could differ from the embodiments shown.

The stents 12, 14 are, in this embodiment, generally annular when viewed in the longitudinal direction of the stent graft 10 and have an undulating, in particular zigzag shape, when viewed in side elevation, as can be seen in FIG. 1, as well as in FIGS. 3 and 4 described below. In this embodiment, the stents 12 and graft tubing 16 are generally cylindrical, that is, they provide a stent graft 10 having a generally uniform and constant diameter along the entire length of the stent graft 10. In other embodiments and devices, the structure may not be cylindrical and could have other shapes. For instance, the structure could be tapered, it could be closed off at one end, or may otherwise have a non-uniform shape.

Each stent 12, 14 is, in this embodiment, a separate element and formed of a wire which is bent into the configuration shown in FIG. 1. More specifically, a length of wire could be bent into an series of zigzag sections or struts, cut to size as necessary, and then curved to bring the two ends together thereby to form an annular ring of zigzag sections. In other embodiments, the stent elements could be formed to the shape shown by cutting a tubing.

The stents 12, 14 may be of a balloon expandable material but are preferably made of a self-expanding material, in particular a shape memory material such as shape memory polymer or alloy. Preferably, the stents 12, 14 are made of nickel titanium alloy, preferably Nitinol.

As can be seen in FIG. 1, the majority of the stents 12, particularly in zone 20 shown in FIG. 1, are substantially aligned such that peaks 22 of the stents 12 extend generally along a common longitudinal line of the stent graft 10 (the variations in the photograph being caused by twisting of the graft material 16). By contrast, a number of the stents 12 are oriented such that respective peaks 22 and valleys 24 are longitudinally aligned with respect to one another, in particular as noted in section 26 of the stent graft 10 shown in FIG.

1. In zone 26, the two adjacent stents 12 have their peaks and valleys, 22 and 24 respectively, aligned so as to opposing one another, thereby to produce what could be described as a frame 30 formed in part from each of the opposing stents 12. In FIG. 1, there are two such frames adjacent one another, the first being denoted by the reference numerals 30 and the second being denoted by the reference numerals 32. These frames 30, 32 delimit respective fenestrations 34, 36, respectively, within the stent graft 10.

In the embodiment shown, the fenestrations 34, 36 are provided with sleeves 38, 40 of graft material, which extend into the volume formed by the graft tubing 16. These sleeves 38, 40 extend, in this example, towards one end 42 of the stent graft 10, which may be the distal or the proximal end of the stent graft 10 when in situ in a patient.

The frames 30, 32 also include, wrapped around the structure of the respective stents 12, a radiopaque coil 44, which in this embodiment extend along the entirety of the portions stent 12 which delimit the frames 30, 32. In the other embodiments, the coil 44 could be disposed on only one of the stent portions 12 delimiting a respective one of the frames 30, 32, although it is preferred that the entirety of the frames 30, 32 be delimited by the radiopaque coil so as to be readily and substantially entirely visible under imaging.

FIG. 1 also shows the provision of additional radiopaque markers 46 on a stent graft 10, which in this example are small tubular lengths of radiopaque material attached to the graft tubing 16 by a suitable suture tie. These additional radiopaque markers 46 indicate radial positions of the stent graft 10 along its longitudinal axis, useful for positioning purposes. The markers 46 are not essential elements to the structure taught herein.

Figure 2:
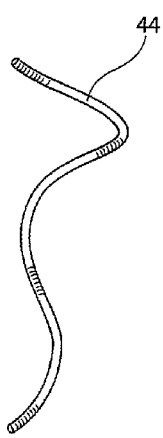
FIG. 2 is a side elevational view of an embodiment of radiopaque marker coil.

Referring now to FIG. 2, there is shown a photograph of a preferred embodiment of radiopaque coil 44. As can be seen in the Figure, the coil is formed of a series of tightly wrapped turns of fine wire which have a pitch such that the adjacent turns touch one another when the coil 44 is in its rest position, that is when it is not bent or folded into a specific configuration. Even so, the structure is preferably such that even when bent in a longitudinal direction, at least a part of each turn is in contact with its adjacent turns of the coil 44.

The coil 44 is in the preferred embodiment made of gold wire, which has excellent biocompatibility characteristics, good radiopaque qualities and is easily conformable given its good ductility. Other embodiments use a coil of silver, platinum or tantalum. In a practical embodiment, the wire forming the coil 44 has a diameter of between 0.05 and 0.5 millimeters, preferably of between 0.1 and 0.2 millimeters and most preferably a diameter of around 0.15 millimeters. This provides satisfactory radiopacity and yet a coil 44 which can easily bend to follow the shape of the underlined stent 12 and which does not impart on the stent 12 any significant restoring force which would materially affect the performance characteristics of the stent 12.

Figure 3:
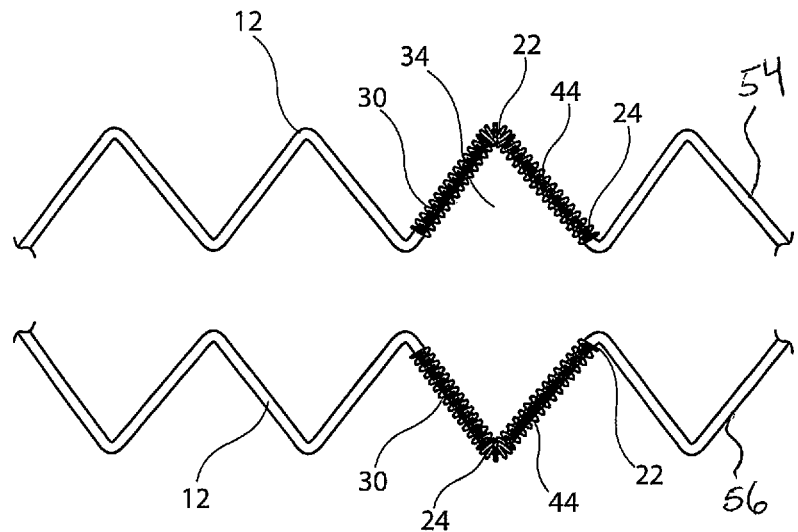
FIG. 3 is an enlarged view of first and second stent elements of the stent graft of FIG. 1.

Referring now to FIG. 3, there is shown in schematic form two of the stents 12 of the stent graft of FIG. 10, showing in better detail the arrangement of coil 44 over the stents 12. As described above, the stents 12 which provide the fenestration 34 are radially arranged such that the peaks and valleys of the two stents 12 are lineally oriented with respect to one another so as to form what can be described as opposing undulating patterns. Of the four openings which can be seen in the example of FIG. 3, one provides a fenestration 34. Of course, others of the openings could provide respective fenestrations should that be desired. Disposed around those portions of the stent 12 which form the frame 30, there are located two coils 44 which delimit the opening to the fenestration 34 in a manner which is opaque to imaging. As described above, the coil 44 is sufficiently flexible that it can bend around the peaks and valleys 22, 24 of the stents 12, at which peaks and valleys 22, 24 the turns of the coil 44 will open slightly on the outside of the radius of curvature.

It is not excluded in other embodiments that there could be provided on each stent 12 two separate lengths of coil 44 which overlie the straight portions of the stents 12 and such that at the peak and valley 22, 24 there is no overlying coil 44. However, in the preferred embodiment there is a single coil 44 over each of the stents 12 at the zone of the frame 30.

As can be seen in FIG. 3, the coils 44 extend over the whole portions of the stents 12 which form the frame 30. In other embodiments coil 44 could be shorter, so as to delimit only a part of the frame 30. It is preferred, however, the whole of the frame 30 is covered with radiopaque coil.

Figure 4:
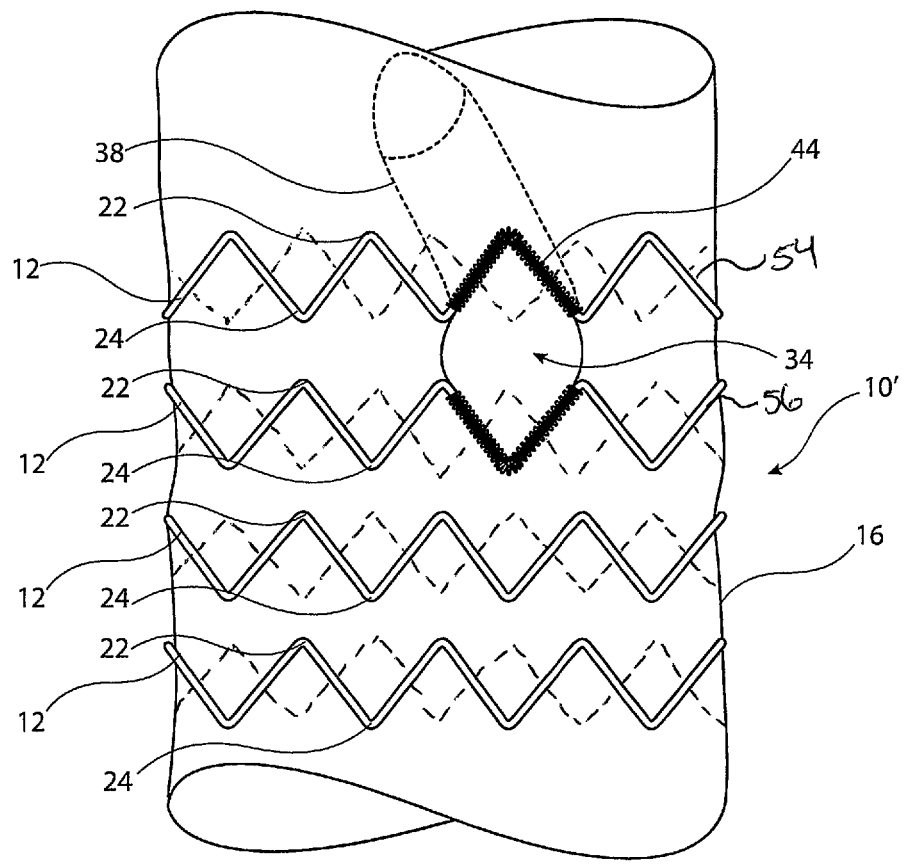
FIG. 4 is a schematic view of the stent assembly of the stent graft of FIG. 1.

Referring now to FIG. 4, there is shown a schematic view of an embodiment of stent graft 10' similar to the stent graft 10 of FIG. 1. Stent graft 10' includes a plurality of zigzag stent rings 12, most of which have respective peak 22 and valleys 24 aligned with one another along the longitudinal axis of the stent graft. On the other hand, the adjacent stents which form the fenestration 34 are arranged such that their respective peaks and valleys are aligned with one another in opposing peak-to-valley alignment rather than peak-to-peak and valley-to-valley alignment as with the other stents. The fenestration 34, also delimited by the wire coil 44, also has a graft sleeve 38 extending into the tube of graft material 16. The sleeve 38 is preferably formed with the graft tubing as a single woven structure. In other embodiments, the sleeve 38 could be formed separately and then secured to, for example by suturing, to the graft tubing 16.

As described above, a plurality of fenestrations could be provided in the stent graft 10, 10' by suitable fenestrations and suitably radially aligned stents 12.

Although the above-described embodiments show stents having a zigzag shape, the teachings herein also encompass other shaped stents, including sinusoidal and other wave shapes. Furthermore, it is not necessary for every stent 12 to have a zigzag or sinusoidal shape. It is envisaged that in some embodiments one or more of the stents 12 could be substantially flat in the longitudinal direction of the stent graft.

The stent graft 10 can readily be manufactured by bending a wire of stent material into a zigzag shape, cutting this into lengths for the stents 12, feeding a suitable length of radiopaque coil 44 over the cut length of wire, curving the wire into an annular ring in the shape of the stent 12, bonding the ends together such as by welding or soldering, thereby to form stents 12 with radiopaque marker coils 44 thereon. Of course, those stents 12 which have no radiopaque marker would omit the step of feeding the coil 44 over the cut stent wire. After formation of the various stents 12, these are then secured, such as by suturing, to the graft tubing 16. The fenestrations 34, 36 will be preformed with a graft tubing 16 and subsequently have attached thereto the sleeves 38, 40, typically by suturing also. In the other embodiments, the sleeves 38, 40 are woven with the principal tubing 16 and then sutured to their respective frames 30, 32 into the final configuration shown in FIG. 1.

It will be appreciated that the structure of stent graft 10, 10' is significantly simpler than prior art fenestrated stent grafts and provides a supported fenestration which makes use of the structure of the stents 12 themselves rather than of a separate strengthening element such as a strengthening ring. Moreover, the fenestrations 34, 36 are able to be radially compressed with the stent graft 10, 10' for delivery by means of an introducer assembly. This can substantially facilitate the delivery of the fenestrated stent graft endoluminally into the patient.

For other implantable medical devices, the stents 12 may have different expanded diameters, rather than being of the same diameter as described above. This can provide a device with a varying outer diameter. Such as structure can be useful in lumens which have a varying inner diameter, for the formation of filters and occluders, and so on.

It is to be understood that the features of the different embodiments described can be combined with one another and that the claims are to be interpreted, even though initially set out in single dependent form, as being combinable as if in multiple dependent form.

What is claimed is:

1. An implantable medical device comprising:
    a longitudinal dimension;
    at least a first and a second stent element disposed in series along the longitudinal dimension of the device, the first and the second stent elements being annular;
    a graft element attached to and extending between the first and the second stent elements;
    a first and a second frame portion comprising portions of the first and the second stent elements, respectively;
    and a fenestration within the graft element, the fenestration extending to and delimited by the first and the second frame portions.

2. An implantable medical device according to claim 1, further comprising a radiopaque material on the first and the second frame portions.

3. A device according to claim 2, wherein at least one of the first and the second stent elements has a wave shape along a circumferential direction, the first and the second frame portions being formed by a part of the wave shape which extends away from the other of the first and the second stent elements.

4. A device according to claim 3, wherein both of the first and the second stent elements have the wave shape along the circumferential direction, the first and the second stent elements being arranged such that a peak and valley are aligned with one another in opposing peak-to-valley alignment, the first and the second frame portions comprised of the portions of the first and the second stent elements at a position at which the peak of the wave shape diverges away from the opposing valley.

5. A device according to claim 3, wherein the first or the second stent element has the wave shape over the entire circumference of the first or the second stent element.

6. A device according to claim 3, wherein both the first and the second stent elements have a wave shape.

7. A device according to claim 1, wherein the fenestration is preformed in the device.

8. A device according to claim 1, including a sleeve of graft material integral with the fenestration.

9. A device according to claim 8, wherein the sleeve of graft material extends into the device.

10. A device according to claim 1 wherein the first and the second stent elements are spaced from one another.

11. A device according to claim 1, further comprising a coil of radiopaque material wound around the first and the second frame portions and made from gold, silver, platinum or tantalum.

12. A device according to claim 1, further comprising a coil of radiopaque material wound around the first and the second frame portions and having a series of adjacent turns that touch one another when the coil is in a rest position.

13. A device according to claim 1, further comprising a coil of radiopaque material wound around the first and the second frame portions and formed of a wire having a diameter of between 0.05 and 0.5 millimeters.

14. A device according to claim 1, wherein the first and the second stent elements are made of a shape memory material.

15. A device according to claim 1, including a second fenestration.

16. An implantable medical device comprising:
    a longitudinal dimension;
    a first and a second stent element being disposed in series along the longitudinal dimension of the device, the first and the second stent elements being annular and adjacent one another;
    the first and the second stent element having a peak and a valley, respectively, aligned longitudinally so as to oppose one another in a peak-to-valley arrangement thereby to produce a first and a second frame portion comprising the peak and the valley respectively;
    a graft element attached to and extending between the first and the second stent elements;
    a fenestration within the graft element, the fenestration extending to and delimited by the first and the second frame portions.

17. An implantable medical device according to claim 16, wherein the first and the second stent elements are spaced from one another.

18. A method of making an implantable medical device, which device includes a longitudinal dimension and a first and a second stent element, the first and the second stent elements being annular, the method including the steps of:
    disposing the first and the second stent elements in series along the longitudinal dimension of the device;
    attaching a graft element to the first and the second stent elements so as to extend therebetween;
    orienting the first and the second stent elements relative to one another such that there is a first and a second frame portion comprising the first and the second stent elements respectively; and
    disposing a coil of radiopaque material around at least a part of the first and the second frame portions, wherein the first and the second frame portions delimit a fenestration in the graft element, and the fenestration extends to the first and the second frame portions.

19. A method according to claim 18, wherein the fenestration is formed by cutting graft material of the device.

20. A method according to claim 18, wherein the step of disposing the coil around at least a part of the first and the second frame portions include: providing at least one of the first and the second stent elements as an annular element, sliding the coil over the at least one stent element, and closing the at least one stent element to form an annular ring with the coil wound thereon.

* * * * *